United States Patent [19]

Saito et al.

[11] Patent Number: 5,323,768

[45] Date of Patent: Jun. 28, 1994

[54] DIATHERMIC DISSECTOR WITH A BIFURCATION HAVING SUBSTANTIALLY THE SAME CROSS-SECTIONAL AREA AS A LUMEN FOR GUIDING A WIRE

[75] Inventors: Tatsuya Saito, Tokyo; Kiyotaka Matsuno, Kunitachi, both of Japan

[73] Assignee: Olympus Optical Co., Ltd., Tokyo, Japan

[21] Appl. No.: 870,923

[22] Filed: Apr. 20, 1992

[30] Foreign Application Priority Data

Apr. 22, 1991 [JP] Japan .................................. 3-090474
Sep. 12, 1991 [JP] Japan .................................. 3-233115

[51] Int. Cl.$^5$ ............................ A61B 1/30; A61B 17/32
[52] U.S. Cl. ............................................ 128/7; 606/47
[58] Field of Search ................. 606/45, 46, 47, 48–51, 606/113, 205; 128/4, 7, 772; 138/118, 111

[56] References Cited

U.S. PATENT DOCUMENTS

| | | | |
|---|---|---|---|
| 3,910,279 | 10/1975 | Okada et al. | 606/47 |
| 4,326,530 | 4/1982 | Fleury, Jr. | 606/47 |
| 4,487,489 | 12/1984 | Takamatsu | 606/47 X |
| 4,529,009 | 7/1985 | Horner et al. | 138/111 |
| 4,911,148 | 3/1990 | Sosnowski et al. | 128/7 X |
| 5,024,617 | 6/1991 | Karpiel | 606/47 |
| 5,035,696 | 7/1991 | Rydell | 606/47 |
| 5,066,295 | 11/1991 | Kozak et al. | 606/47 |
| 5,084,054 | 1/1992 | Bencini et al. | 606/113 |
| 5,163,938 | 11/1992 | Kambara et al. | 606/47 |

FOREIGN PATENT DOCUMENTS 61-156911 9/1986 Japan .
64-32854 2/1989 Japan .

Primary Examiner—Richard J. Apley
Assistant Examiner—Karen A. Jalbert
Attorney, Agent, or Firm—Armstrong, Westerman, Hattori, McLeland & Naughton

[57] ABSTRACT

According to the present invention, a sheath has flexibility, and includes a first lumen for guiding a conducting wire in the sheath and a second lumen for injecting contrast medium, which are made of insulating material. The wire exposes itself outside at openings formed in the terminal position of the first lumen, and thus forms a dissecting section for dissecting a contact tissue with supplied high-frequency current. The proximal portion of the sheath is connected to a bifurcating section for bifurcating the sheath into a first path having substantially the same cross-sectional area as the first lumen and communicating with the first lumen for guiding the wire so that the wire will not buckle up and a second path communicating with the second lumen. An operation handle for advancing or withdrawing the wire is connected externally to the back of the first path.

30 Claims, 11 Drawing Sheets

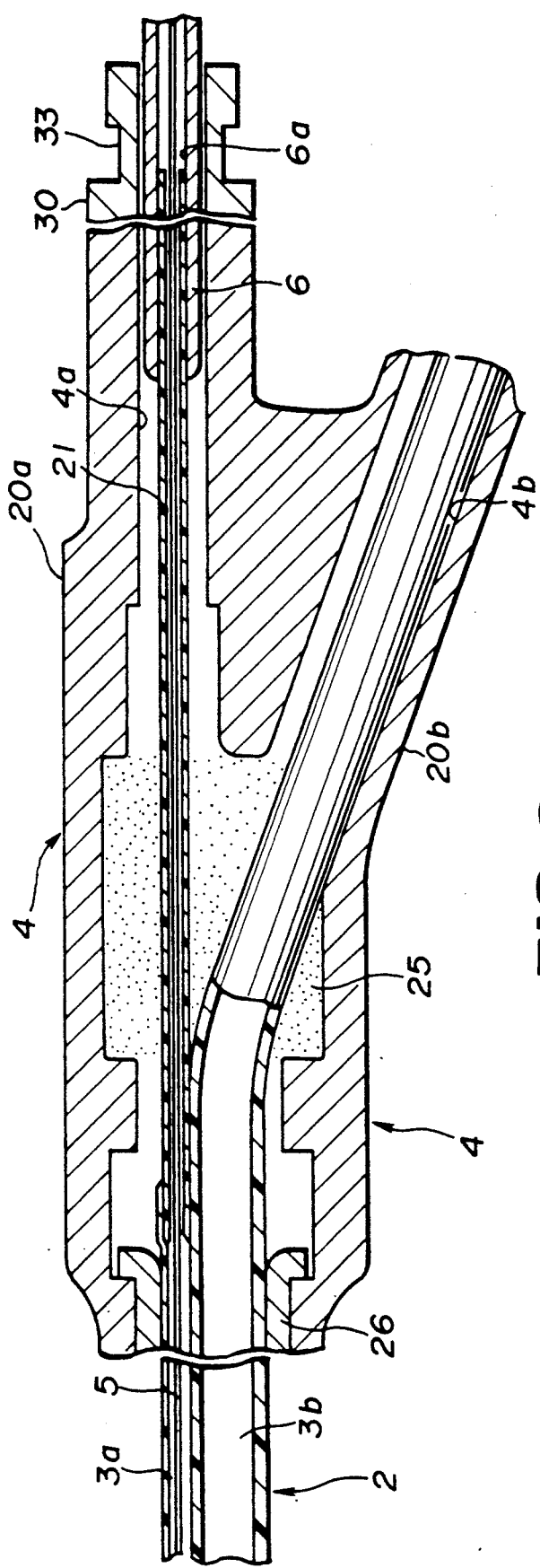

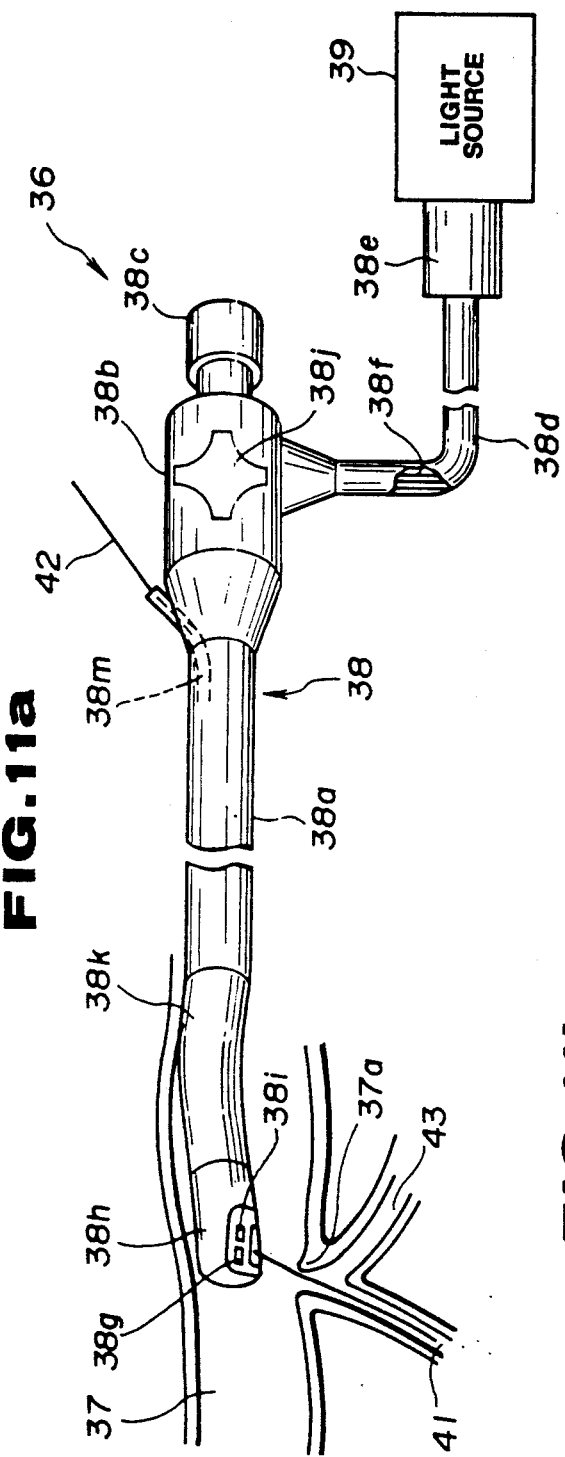
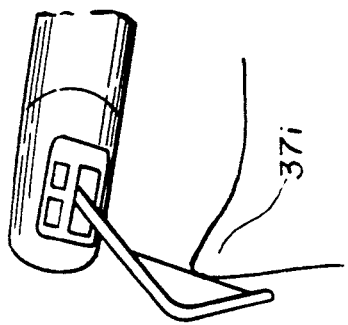
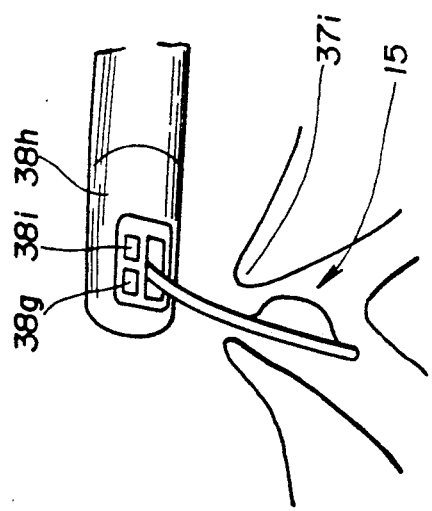

DIATHERMIC DISSECTOR WITH A BIFURCATION HAVING SUBSTANTIALLY THE SAME CROSS-SECTIONAL AREA AS A LUMEN FOR GUIDING A WIRE

BACKGROUND OF THE INVENTION

1. FIELD OF THE INVENTION

The present invention relates to a diathermic dissector for dissecting living tissues by flowing high-frequency current over a wire, or more particularly, to a diathermic dissector with a bifurcation forming a path having substantially the same cross-sectional area as a lumen for guiding a wire.

2. DESCRIPTION OF THE RELATED ART

Diathermic dissectors for endoscopes have been employed in recent years. Herein, an insertion tube of an endoscope is guided to a body cavity, a flexible sheath characteristic of electric insulation is routed through a channel formed in the insertion tube, a diathermic dissecting section formed with a conducting wire exposed at the tip of the flexible sheath is pressed on a therapeutic region, then high-frequency current is supplied to flow through the conducting wire to dissect an intended living tissue.

Of the foregoing diathermic dissectors, an endoscope diathermic dissector disclosed in Japanese Unexamined Utility Model No. 61-156911 is well-known. FIG. 1 shows the distal portion of the endoscope diathermic dissector.

In FIG. 1, on a side wall in the terminal (distal) portion of a flexible sheath 91 made of electrically-insulating material, a pair of openings or side holes 92a and 92b are bored in the longitudinal-dislocated manner to penetrate through a first lumen 93 for guiding a wire. A conducting wire 94 is routed through these side holes 92a and 92b so that the conducting wire 94 will come out of the flexible sheath 91 between the side hole 92a and the side hole 92b. The exposed portion of the conducting wire 94 forms a diathermic dissecting section 95.

The tip of the wire 94 is provided with a locking member 96. With the locking member 96, the wire 94 is locked in the distal end of the first lumen 93. As shown in FIGS. 1 and 2, the flexible sheath 91 has a second lumen 97 running in parallel with the first lumen 93, allowing a guide wire, which is not shown, or other guide member to pass through, and serving as a fluid feed path for feeding contrast medium.

As shown in FIG. 3, the proximal end of the flexible sheath 91 is connected to a bifurcating section 98 for bifurcating the flexible sheath into a first duct 98a for guiding the wire 94 and a second duct 98b connected to the second lumen 97. A base 99 is attached to the end of the second duct 98b.

The wire 94 is connected to an operation member, which is not shown, at the back of the first duct 98a from which the wire 94 comes out. When the operation member is advanced or withdrawn, a dissecting section 95 of the wire 94 projects or part of the sheath in which the dissecting section 95 is formed bends. A wire exposing itself outside at the opening is pressed onto a tissue of a therapeutic region. With high-frequency current supplied by surgeon's manipulation, the tissue is cauterized and dissected.

To feed contrast medium through the second lumen 97, a syringe (not shown) must be mounted on the base 99.

In an endoscope diathermic dissector having the aforesaid configuration, when a therapeutic region is to be dissected, an operation member is advanced or withdrawn to expose a wire 94 of a dissecting section 95 or project the corresponding portion of a sheath so that the wire will touch the therapeutic region.

In the aforesaid configuration of prior art, a space 100 of a first duct 98a for guiding a wire 94 is so large that even when an operation member is, for example, advanced, the wire 94 buckles up in the large space 100 (as shown with an alternate long and two short dashes line in FIG. 3).

Therefore, advancement by a surgeon's manipulations is not fully communicated to the distal end of the wire 94. As a result, the dissecting wire section exposed outside at the opening cannot be projected to form a shape most suitable for dissection. This results in insufficient operability. When a wire buckles up, the wire must be stretched (withdrawn) once, then advanced.

When buckling occurs, even if the wire 94 is stretched, bending distortion cannot be dissolved quickly. Advancement and withdrawal must be repeated to shape the wire as desired. When advancement and withdrawal are repeated, buckling often recurs. When buckling is repeated, great distortion occurs in the buckled area. The wire 94 becomes prone to rupture, deteriorating durability.

In other cases, when an operation member is withdrawn, the distal portion of a sheath 91 in which a dissecting section 95 is formed is curved to form an arc. This allows a portion of a wire 94 exposing itself outside or the dissecting section 95 to project for use in dissecting an object tissue. After dissection is complete, the operation member must be advanced to straighten the curved area. During the advancement, the wire 94 of prior art buckles up in a large space 100 as described above. This results in degraded operability and deteriorated durability of the wire 94.

During cleaning, the operation member is advanced and withdrawn repeatedly. In prior art, the cleaning causes the wire 94 to buckle up in the large space 100 as described previously.

SUMMARY OF THE INVENTION

The object of the present invention is to provide a diathermic dissector offering high operability and permitting reliable transmission of a manipulation force to a dissecting section without buckling even a small-diameter operation wire.

Another object of the present invention is to provide a diathermic dissector capable of preventing deterioration of durability of an operation wire.

The diathermic dissector comprising a sheath having flexibility and including a first lumen and a second lumen which are made of insulation material, a conducting wire running through the first lumen, exposing itself outside at openings formed in the terminal portion of the first lumen, and forming a dissecting section for dissecting a contact tissue with supplied high-frequency current, a bifurcating section formed in the proximal portion of the sheath to bifurcate the sheath into a first path having substantially the same cross-sectional area as the first lumen and communicating with the first lumen and a second path communicating with the second lumen, and an operation member connected to the proximal portion of the wire for advancing or withdrawing the wire in the longitudinal direction of the sheath. The cross-sectional area of the first path branching out at the bifurcating section and communicating with the first lumen is substantially the same as that of the first lumen. Therefore, even when the operation member is advanced or withdrawn, the wire will not buckle up in the first path.

BRIEF DESCRIPTION OF THE DRAWINGS

FIG. 2 is a 2—2 cross-sectional diagram of FIG. 1;

FIG. 3 is a cross-sectional diagram of a bifurcating section in the proximal portion of the diathermic dissector of prior art;

FIGS. 4 to 11 relate to the first embodiment of the present invention;

FIG. 4 is a configuration diagram of an entire diathermic dissector of the first embodiment;

FIG. 5 is a cross-sectional diagram of a main unit of the diathermic dissector;

FIG. 6 is an a 6—6 cross-sectional diagram of FIG. 5;

FIG. 7 is a cross-sectional diagram of a bifurcating section in the proximal portion of the diathermic dissector;

FIG. 8 is a cross-sectional diagram of a locking member for locking a wire;

FIG. 9 is a cross-sectional diagram showing the proximal portion of an operation pipe;

FIG. 10 is an explanatory diagram of a variant of the distal portion of a sheath in the first embodiment;

FIGS. 11a, 11b, and 11c are explanatory diagrams for dissection using the diathermic dissector;

FIG. 15 is a lateral view showing the appearance of a main unit of a diathermic dissector in the fifth embodiment;

FIG. 16 shows an enlarged 16—16 cross section of FIG. 15;

FIG. 17 is a cross-sectional diagram showing the distal portion of a sheath;

FIG. 18 is an overall configuration diagram of the fifth embodiment;

FIG. 19 is a cross-sectional diagram showing the configuration of a bifurcating section;

FIG. 20 shows an enlarge 20—20 cross section of FIG. 19;

FIG. 21 is an explanatory diagram for dissection;

FIG. 22 is a cross-sectional diagram of the distal portion of a sheath in a variant of the fifth embodiment.

BRIEF DESCRIPTION OF THE PREFERRED EMBODIMENTS

Figure 1:
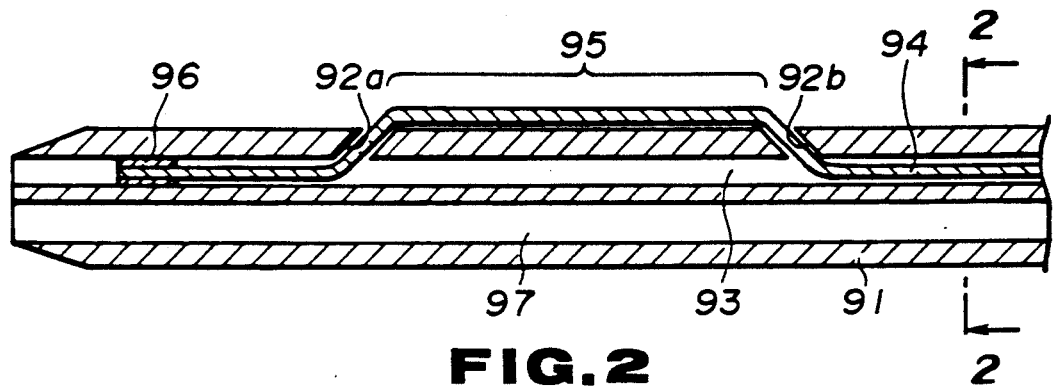
FIGS. 1 to 3 are cross-sectional diagrams of the distal portion of a diathermic dissector of prior art.
Figure 2:
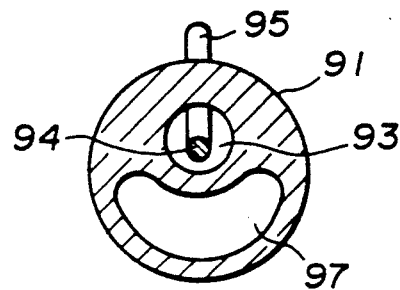
Figure 3:
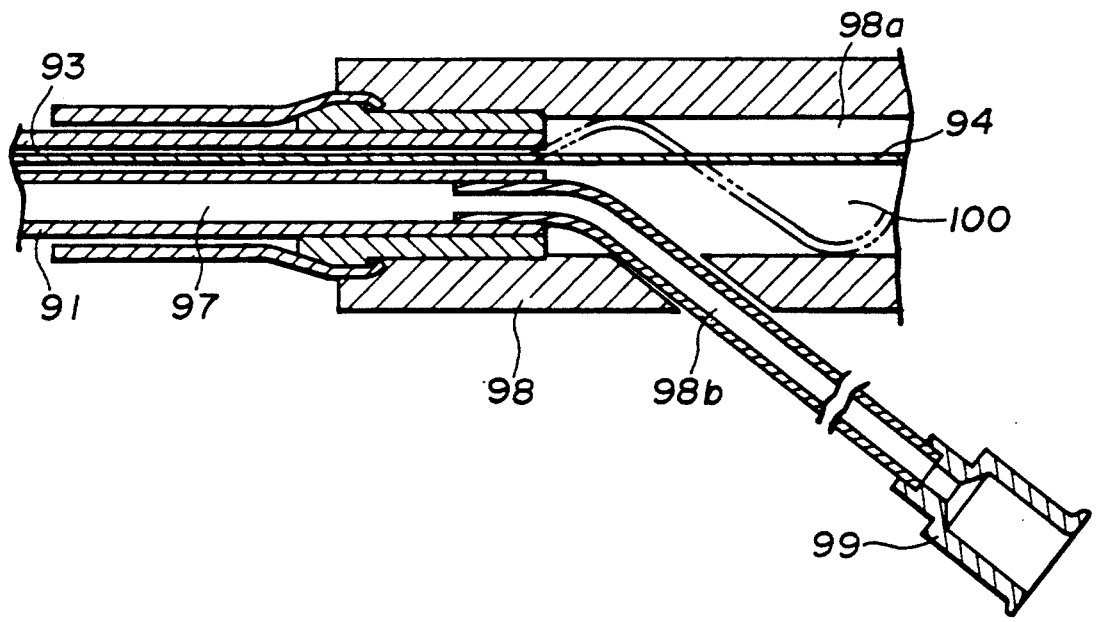
Figure 4:
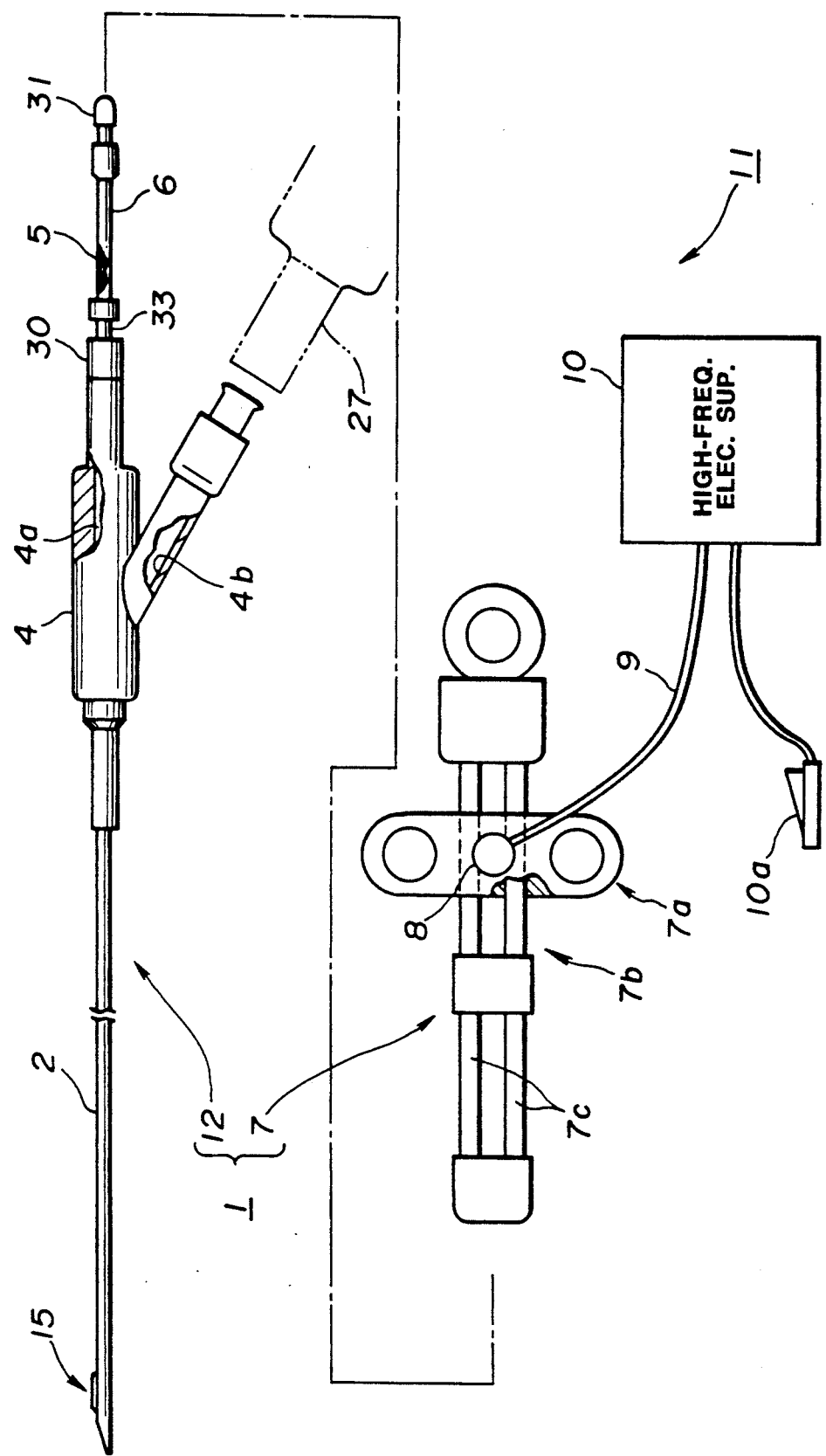

As shown in FIG. 4, an endoscope diathermic dissector 1 of the first embodiment comprises a flexible sheath 2 characteristic of electric insulation, a bifurcating section 4 formed in the back (proximal) portion of the flexible sheath 2 for bifurcating the flexible sheath 2 into a first duct 4a and a second duct 4b, a wire 5 characteristic of electric conduction, used for dissection, and routed through a first lumen 3a (see FIG. 5) formed in the flexible sheath 2 and the first duct 4a, an operation (sliding) pipe 6 extending from the proximal end of the first duct 4a to be connected to the proximal end of the dissection wire 5, and an operation handle 7 connected to the proximal ends of the first duct 4a and the operation pipe 6 to be detached freely.

A connector 8 formed on the operation handle 7 is connected to a high-frequency power supply 10 for supplying high-frequency current via a cable 9. Supply of high-frequency current can be turned on or off using a foot switch connected to the high-frequency power supply 10.

The diathermic dissector 1 and high-frequency power supply 10 form a high-frequency dissecting apparatus 11.

Figure 5:
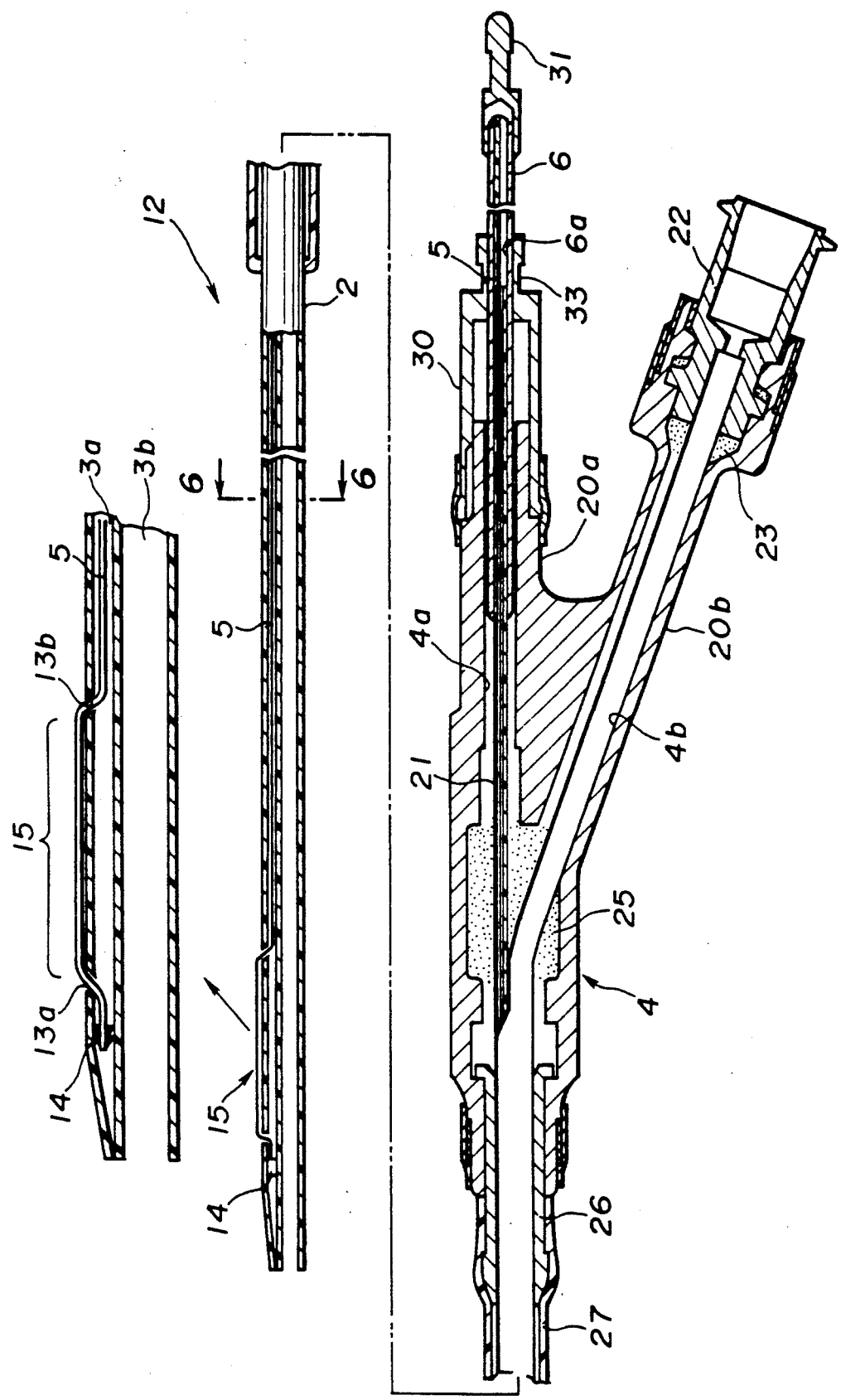

FIG. 5 shows a main unit 12 of a high-frequency dissector from which an operation handle 7 is removed. As shown in FIGS. 5 and 6, in a flexible sheath 2, a first lumen 3a for guiding a wire and a second lumen 3b for therapeutic use are adjoining each other. A wire 5 is running through the first lumen 3a. The cross-sectional area of the second lumen 3b is larger than that of the first lumen 3a, so that contrast medium or biochemical fluid can flow smoothly.

As shown in FIG. 5, on the side wall of the distal portion of the flexible sheath 2, a pair of openings or side holes 13a and 13b are bored to penetrate through a first lumen 3a in a longitudinally-dislocated manner. Then, a wire 5 routed to the first lumen 3a runs through the side hole 13b to expose itself outside, then enters the side hole 13a to lie in the first lumen 3a. Then, the wire 5 is locked near the end of the first lumen 3a with a locking member 14 attached to the end of the wire 5.

To short, the wire 5 is routed so that it will come out of the flexible sheath 2 only between the two side holes 13a and 13b. The exposed portion of the wire 5 forms a high-frequency dissecting section 15. As shown in FIG. 6, the dissecting section 15 is formed on a line linking the centers of the first lumen 3a and second lumen 3b on the opposite side of the second lumen 3b.

Figure 8:
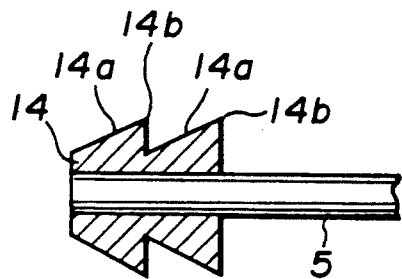

The locking member 14 has multiple (two in this embodiment) shades 14a whose outer diameters are larger than the inner diameter of the lumen 3a as shown in FIG. 8. In the locking member 14, the edge 14b of each shade 14a is oriented to the direction of pulling the wire 5 (to the proximal portion) and locked in the first lumen 3a distal to the side hole 13a.

The first lumen 3a on the distal side of the flexible sheath 2 is tapered to be blocked. The second lumen 3b opens on the end plane of the sheath 2.

As shown in FIGS. 5 and 7, the proximal portion of a flexible sheath 2 is connected to a bifurcating section 4 at which a first duct 4a and a second duct 4b for therapeutic use are branching out with a certain angle. This bifurcating section 4 includes, for example, a linear extension 20a extending linearly and forming the first duct 4a and a branch 20b extending obliquely to the first duct 4a from the confluence in the distal portion and forming the second duct 4b. The bifurcating section 4 is made of plastic or other insulating material, or metal coated with insulating material, or other nonconducting metal.

In the bifurcating section 4, part of the back of the flexible sheath 2 corresponding to the first lumen 3a (upper part of the sheath 2 in FIG. 5) is cut out so that the first lumen 3a will open externally. The tip of a guide pipe 21 is pressed into the opening to prevent the wire 5 from buckling up. Thus, the guide pipe 21 is connected to communicate with the first lumen 3a. The guide pipe 21 is, for example, a circular pipe made of plastic or other insulating material to be more rigid than the sheath 2, and routed through the first duct 4a linearly.

The guide pipe 21 is pressed into the first lumen 3a. The inner diameter of the guide pipe 21 is larger by the thickness of the pipe 21 than that of the first lumen 3a (since the guide pipe 21 is pressed into the first lumen 3a by widening the inner circumference of the first lumen 3a, the inner diameter of the guide pipe 21 can be larger by the thickness of the guide pipe 21 than that of the first lumen 3a).

Since the inner diameter of the guide pipe 21 is almost equal to that of the first lumen 3a, the wire 5 running through the guide pipe 21 does not buckle up in the guide pipe 21 (for the same reason that the wire 5 does not buckle up in the first lumen 3a) when the wire 5 is advanced or withdrawn. That is to say, the guide pipe 21 helps remove a space causing the wire 5 to buckle in a duct 4a in a bifurcating section 4 or restrict movement of the wire 5 so that the wire 5 will not buckle up (restrict movement of the wire 5 in the direction perpendicular to the axis of the duct 4a).

Part of the back of the sheath 2 corresponding to the first lumen 3a is cut out, and that corresponding to the second lumen 3b is routed through a second duct 4b in a branch 20b extending obliquely. At the back of the sheath 2 running through the second duct 4b, a base 22 is adhered to the end of the branch 20b with bond 23. A syringe 24 FIG. 18 for injecting contrast medium can be mounted on the base 22. Moreover, a guide wire (See FIG. 11a) can be inserted through the base 22.

In the bifurcating section 4, a bifurcation from which the first duct 4a and second duct 4b are branching is filled with bond 25 and thereby reinforced.

Part of the outer circumference of the sheath 2, which is located forward to the connection of the guide pipe, is provided with a sheath coupler 26. The sheath coupler 26 connects the back of a break-prevention tube 27 with the tip of a bifurcating section 4.

The guide pipe 21 extends into, for example, a handle joint 30 clamped on the back of a linear extension 20a. The handle joint 30 is connected with the tip of an operation handle 7.

Figure 9:
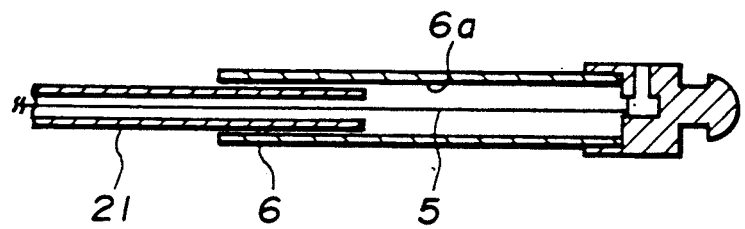

As shown in FIGS. 7 and 9, an operation pipe 6 having a lumen 6a is mounted on the outer circumference of the guide pipe 21, so that the operation pipe 6 can slide on the circumferential surface of the guide pipe 21 to advance or withdraw. The operation pipe 6 is formed with, for example, a metallic pipe. The back portion of the operation pipe 6 is projecting beyond a handle joint 30.

The back portion of a wire 5 running through the guide pipe 21 lies in the operation pipe 6. An electrode 31 attached to a slider 7a forming an operation handle 7 is soldered or silver-soldered to the back of the operation pipe 6. The electrode 31 has an irregular shape, which is fitted into a ditch, which is not shown, of the slider 7a and screwed up.

In FIG. 4, an operation handle 7 includes a slider 7a having guide holes through which guide bars 7c of a handle body 7b are running, wherein the slider 7a can slide towards or away from the handle body 7b.

The operation handle 7 is connected to a main unit 12 of a diathermic dissector. When the slider 7a is moved towards or away from the operation handle body 7b, the distal portion of the operation pipe 6 slides back and forth on the circumferential surface of the guide pipe 21 within a linear extension 20a. For example, when the slider 7a is advanced to a foremost position, the tip of the operation pipe 6 advances to the vicinity of an area filled with bond 25.

A handle joint 30 connecting the flexible sheath 2 with the operation handle 7 has a recess 33 allowing the operation handle 7 to rotate freely.

Figure 10:
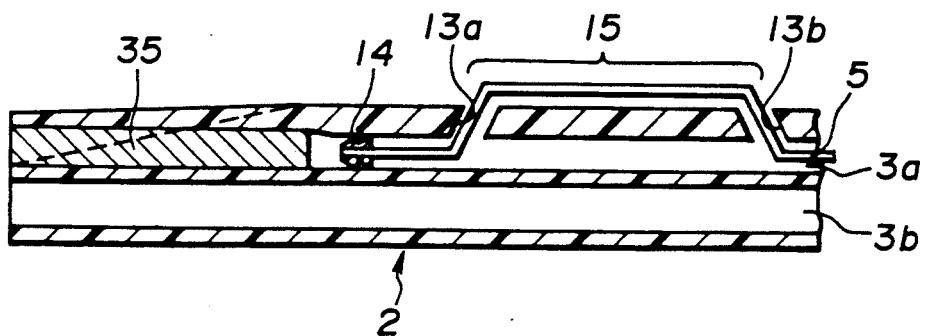

To block the tip of a first lumen 3a for guiding a wire, as shown in FIG. 10, a resin blocking member 35 may be inserted to the tip of the first lumen 3a, then part of the flexible sheath 2 corresponding to the first lumen 3a may be tapered as indicated with a dash line to lock the blocking member 35 in the first lumen 3a.

The operation of the first embodiment having the aforesaid configuration will be described.

Dissecting the duodenal papilla using an endoscope apparatus 36 shown in FIGS. 11a, 11b and 11c will be described as an example of treatment using a diathermic dissector 1. The endoscope apparatus 36 comprises a fiberscope 38, a light source for supplying illumination light to a propagation means for propagating illumination light through the fiberscope 38, and the diathermic dissector 1 or other treatment adapter.

First, as shown in FIG. 11a, the fiberscope 38 or other endoscope is guided in a body cavity. Then, the distal portion of an insertion tube 38a is guided to the vicinity of the papilla 37i of the duodenum 37.

The fiberscope 38 comprises an elongated insertion tube 38a, an operation unit 38b formed at the back of the insertion tube 38a, an eyepiece unit 38c formed at the back of the operation unit 38b, and a light guide cable 38d extending outside from the operation unit 38b.

When a connector 38e attached to the tip of the light guide cable 38d is connected to the light source 39, illumination light incident on one end surface of a light guide 38f formed with a fiber bundle is propagated and emitted from an illumination window 38g on which other end surface of the light guide 38f is arranged.

In a distal end 38h having the illumination window 38g, an observation window 38i is formed adjacently to the illumination window 38g. An objective installed in the observation window 38i forms an optical image on the distal end surface of an image guide. Passing through the image guide, the optical image comes to the other end surface in the eyepiece unit 38c. The optical image can be observed in an enlarged scale through an eyepiece in the eyepiece unit 38c. The operation unit 38b is provided with angulation knob 38j. The angulation knob 38j is used to bend a bending section 38k adjoining the distal end 38h. Moreover, an inlet of a channel 38m is formed near the proximal end of the insertion tube 38a. Various treatment adapters can be inserted through the inlet to project the distal portions of the treatment adapters from an outlet of the distal end 38h.

After the distal portion of an insertion tube 38a is guided to the vicinity of the papilla 37a, a contrast medium tube, which is not shown, is routed through a channel 38m and guided to the bile duct 41. Then, contrast medium is injected to the bile duct 41 via the contrast medium tube. With injection of contrast medium, the position of the bile duct 41 can be identified using an X-ray apparatus.

After injection of contrast medium, a guide wire 42 is routed through a duct for contrast medium or for the contrast medium tube and guided to the bile duct 41. With the guide wire 42 left in the bile duct 41, the contrast medium tube is removed. At this time, the contrast medium tube must be removed with the guide wire 42 kept stationary, so that the guide wire 42 will not come off from the bile duct 41. FIG. 11a shows the state. (The guide wire 42 for use in this dissection therapy should be at least twice as long as the contrast medium tube.) In FIG. 11a, 43 denotes the common bile duct.

Next, a diathermic dissector 1 is guided to the bile duct 41 with the help of the guide wire 42 left intact in the bile duct. Specifically, the tip of the therapeutic lumen 3b of a flexible sheath 2 is fitted to the proximal end of the guide wire 42. Then, the guide wire 42 is kept stationary so that it will not come off from the bile duct 41. Then, the flexible sheath 2 is routed through the channel 38m of the fiberscope 38. When the tip of the flexible sheath 2 has been guided in the bile duct 41, the guide wire 42 is removed.

Then, a slider 7a of an operation handle 7 is, for example, advanced, so that a wire 5 as well as an operation pipe will advance. Since the tip of the wire 5 is fixed, the wire 5 projects from two side holes 13a and 13b. In this embodiment, a first lumen 3a is connected to a guide pipe 21 having substantially the same inner diameter as the first lumen 3a in a bifurcating section 4. Therefore, the wire 5 will not buckle up but advance through the guide pipe 21. That is, the cross-sectional area of a path for the wire 5 is large enough for the wire 5 to advance or withdraw. The guide pipe 21 does not have a space allowing the wire 5 to bend. Therefore, the wire 5 advances or withdraws when the operation handle 7 is advanced or withdrawn.

Part of the wire 5 projecting from the two side holes 13a and 13b, or a diathermic dissecting section 1, is pressed on the papilla 37i as shown in FIG. 11b. In this state, a foot switch 10a is stepped down to flow high-frequency current through the wire 5. Thus, the papilla 37a can be dissected.

When a slider 7a of an operation handle 7 is, for example, withdrawn, part of a sheath 2 or a dissecting section 15 may be curved to form an arc as shown in FIG. 11c. Thereby, a wire 5 of the dissecting section 15 is shaped like a knife. Then, dissection is carried out. After dissection, the slider 7a of the operation handle 7 is advanced. This allows the wire 5 to return to the initial state (state shown in FIG. 5) without buckling.

In this embodiment, a wire 5 runs through a path having an almost constant cross-sectional area from the tip of a flexible sheath 2 through a bifurcating section 4 to a fixture for securing a guide pipe 21 and an operation pipe 6. This prevents the wire 5 from bending in the middle.

A diathermic dissector of prior art has a large outer diameter for structural reasons. Therefore, after a contrast medium tube is removed from the bile duct 41, the diathermic dissector cannot be routed to the bile duct 41. By making the most of a guide wire 42 as described in this embodiment, the diathermic dissector can be routed to the bile duct 41 effortlessly and reliably.

Furthermore, since the tip of a first lumen 3a for guiding the wire 5 is blocked, invasion of body fluid or bacteria into the first lumen 3a can be prevented. This results in improved hygiene and upgraded maintainability.

A locking member 14 having multiple shades is used as a means for locking the wire 5 in the tip of the first lumen 3a. Therefore, the wire 5 can be locked in the first lumen 3a reliably.

Furthermore, a bifurcating section 4 in the proximal portion of the flexible sheath 2 rotates freely in association with the operation handle 7. This improves operability in mounting or demounting a syringe 27 on or from a base 22 at the proximal end of a second duct 4b for therapeutic use. Consequently, the operability of a diathermic dissector 1 is improved.

Figure 12:
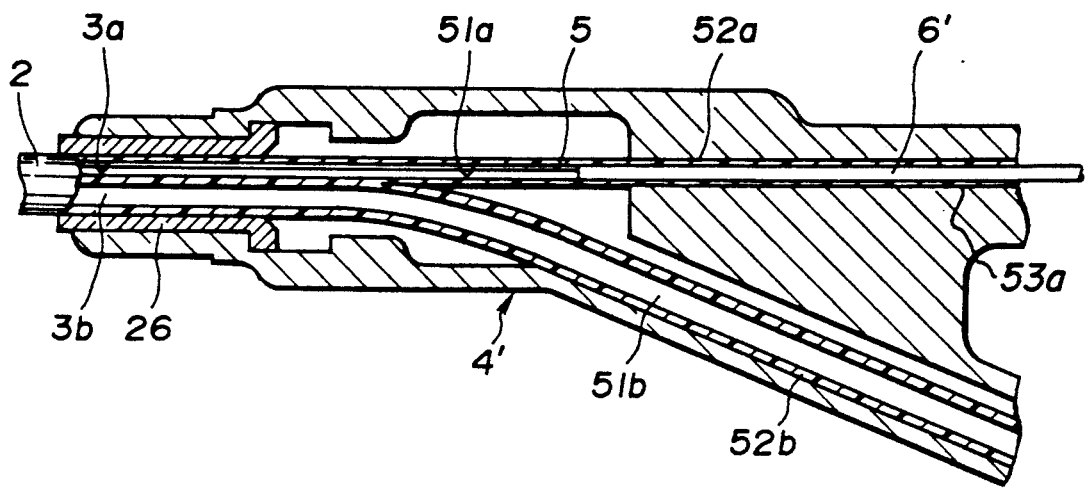
FIG. 12 is a cross-sectional diagram showing the configuration of a bifurcating section in the second embodiment of the present invention.

FIG. 12 shows the configuration of a bifurcating section 4' in the second embodiment of the present invention. A modified internal configuration of a bifurcating section 4 in the first embodiment is implemented in the second embodiment. A flexible sheath 2 having two lumens 3a and 3b is bifurcated into two tubes 52a and 52b having paths 51a and 51b respectively in a bifurcating section 4'.

A flexible sheath 2 is fixed to the tip of a bifurcating section 4' using a sheath coupler 26. The flexible sheath 2 is bifurcated into a tube 52a having a first path 51a communicating with a first lumen 3a in the vicinity of the back of the sheath coupler 26 and a tube 52b having a second path 51b communicating with a second lumen 3b.

The tube 52a extends in the longitudinal direction of the sheath 2 and runs through a duct 53a of a linear extension 20a in the bifurcating section 4'. The inner diameter of the duct 53a is substantially equal to the outer diameter of the tube 52a (except a portion at which the sheath is bifurcating into the two tubes 52a and 52b). An operation pipe 6' is routed through the first path 51a formed with the tube 52a. A wire 5 running through the first lumen 3a is routed through the operation pipe 6'. The back of the wire 5 is fixed to the back of the operation pipe 6'. Other components are almost identical to those of the first embodiment.

The operation and effects of this embodiment are substantially the same as those of the first embodiment.

Figure 13:
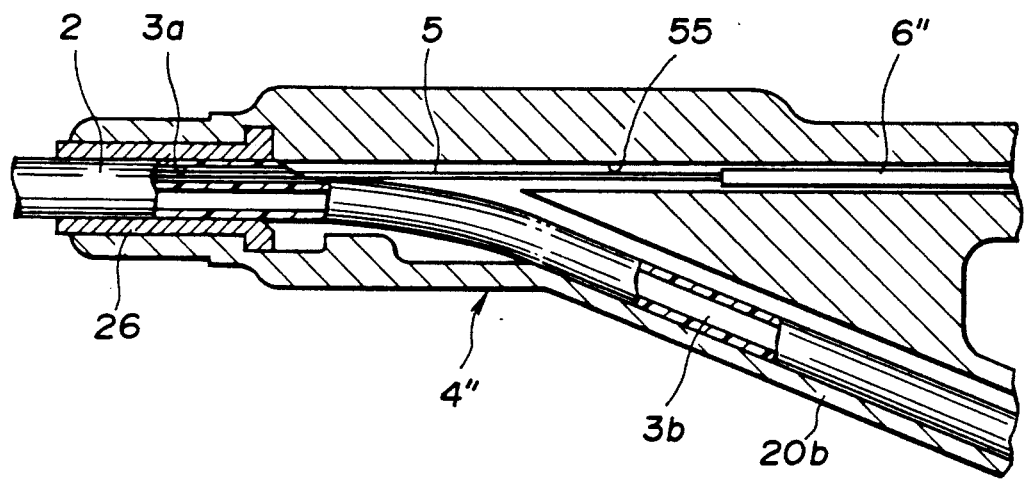
FIG. 13 is a cross-sectional diagram showing the configuration of a bifurcating section in the third embodiment of the present invention.

FIG. 13 shows the configuration of a bifurcating section 4" in the third embodiment of the present invention. A modified internal configuration of a bifurcating section in the first embodiment is implemented in the third embodiment. A flexible sheath 2 having two lumens 3a and 3b is fixed to the tip of the bifurcating section 4" using a sheath coupler 26. Part of the flexible sheath 2 corresponding to a first lumen 3a is cut out in the vicinity of the back of the sheath coupler 26, and extending obliquely backward from the vicinity of the back of the sheath coupler 26. Thus, only a second lumen 3b is branching and running through a branch 20b (extending obliquely backward).

From the cut opening of the sheath 2, the wire 5 running through the first lumen 3a enters a guide groove 55 or a hollow path formed in the direction in which the first lumen 3a would extend. The distal portion of an operation pipe 6" is routed through the guide groove 55. That is to say, the guide groove 55 is formed in a hollow path having a cross-sectional area large enough to pass the operation pipe 6". The outer diameter of the operation pipe 6" is substantially the same as, for example, the inner diameter of the first lumen 3a. Eventually, the cross-sectional area of the guide groove 55 is almost equal to that of the first lumen 3a.

In this embodiment, the diameter of a guide groove 55 formed in a bifurcating section 4" is set to a minimum size allowing an operation pipe 6" to slide freely. When the operation pipe 6" is advanced or withdrawn, a wire 5 advances or withdraws without bending in the guide groove 55 or operation pipe 6". Other components are identical to those of the first embodiment.

According to this embodiment, a guide groove 55 realizes a facility similar to a guide pipe 21 stated in the first embodiment. Therefore, the diameter of an operation pipe 6" can be further reduced (in the first embodiment, the inner diameter of an operation pipe 6 must be larger than the outer diameter of the guide pipe 21). Moreover, bending of a wire 5 can be minimized. Consequently, occurrence of buckling or sagging can be minimized, allowing an operation handle to advance or withdraw reliably.

Figure 14:
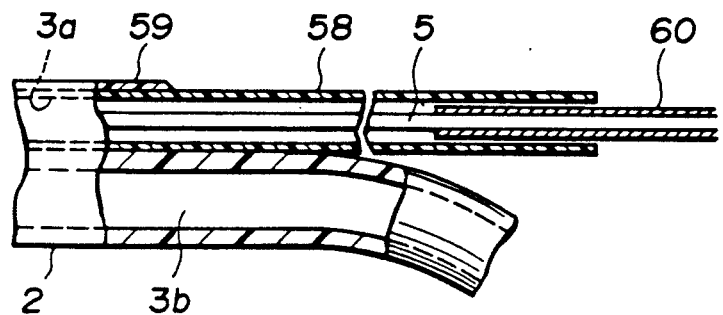
FIG. 14 is a cross-sectional diagram showing the configuration of the inside of a bifurcating section in the fourth embodiment of the present invention.

FIG. 14 shows the internal configuration of a bifurcating section in the fourth embodiment of the present invention. A modified internal configuration of a bifurcating section 4 in the first embodiment is implemented in this fourth embodiment. A flexible sheath 2 having two lumens 3a and 3b is fixed to the tip of a bifurcating section using a sheath coupler. Part of the flexible sheath 2 corresponding to a first lumen 3a is cut out in the vicinity of the back of the sheath coupler. A second lumen 36 is extending obliquely backward from the vicinity of the back of the sheath coupler.

The tip of a guide pipe 58 is fitted into the cut part of the flexible sheath 2 corresponding to the first lumen 3a. The fitting section is secured with bond 59. The guide pipe 58 extends in the direction in which the first lumen 3a would extend. A wire 5 is routed through the guide pipe 58. An operation pipe 60 through which the wire 5 is running is also routed through the guide pipe 59 to slide freely.

This embodiment is characterized by the operation pipe 60 which is routed through the guide pipe 58 to slide freely. Other components are identical to those of the first embodiment. The operation and effects are substantially the same as those of the first embodiment.

Figure 15:
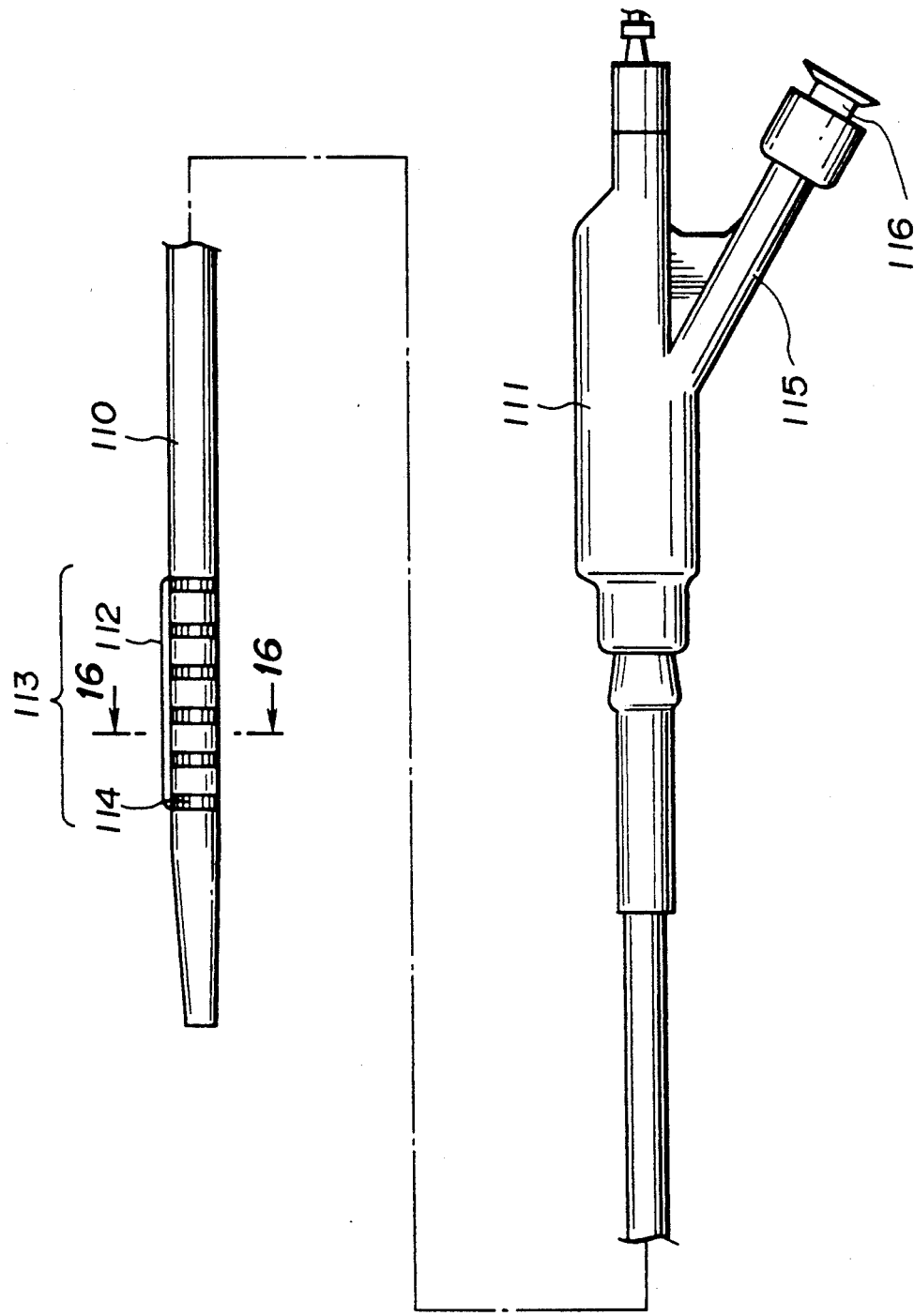
FIGS. 15 to 22 relate to the fifth embodiment of the present invention.

FIG. 15 shows a diathermic dissector of the fifth embodiment of the present invention. The proximal portion of a flexible sheath 110 formed with a perforated tube characteristic of electric insulation is connected to a bifurcating section 111. The end of a branch 115 of the bifurcating section 111 is provided with a base 116 on which a syringe, which is not shown, can be mounted.

In the distal portion of the flexible sheath 110, a knife wire 112 or a dissecting section is coming out from the flexible sheath 110. In the dissecting section 113 of the flexible sheath 110 or the knife wire 112, marks 114 are made at regular intervals on the flexible sheath 110. These marks help measure lengths or sizes of object tissues.

Figure 16:
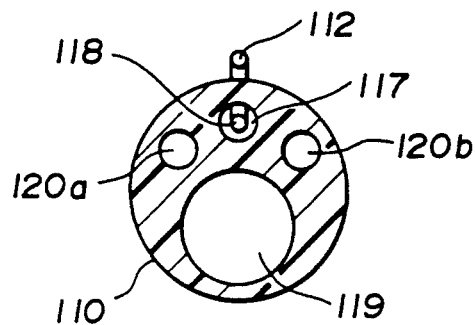
Figure 17:
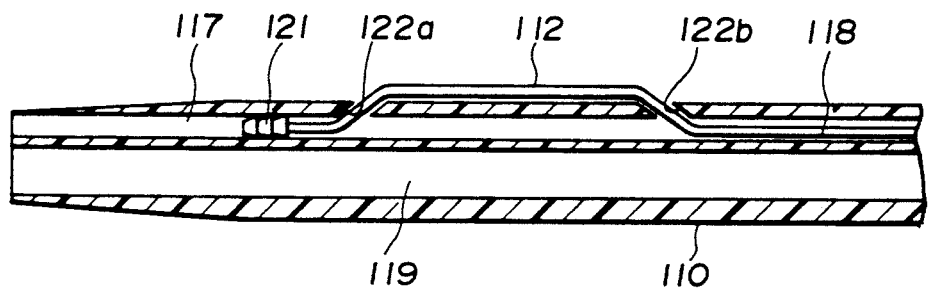

As shown in FIG. 16 or 17, the flexible sheath 110 has a first lumen 117 for guiding a conducting wire 118, and a second lumen 119 having a larger diameter than the first lumen 117, running in parallel with the first lumen 117, allowing a guide wire or other guide member, which is not shown, to pass through, and serving as a path for feeding contrast media or other fluid.

As shown in FIG. 16, in addition to the first lumen 117 and the second lumen 119, two lumens 120a and 120b are bored through the wall of a sheath 2. This improves flexibility of the sheath 110. These two lumens 120a and 120b are formed symmetrically with respect to a line linking between the centers of the first lumen 117 and second lumen 119.

As shown in FIG. 17, a locking member 121 having stoppers on the outer circumference is adhered to the distal lateral end of a wire 118. The locking member 121 is locked in the first lumen 117 on the distal side of wire extraction holes 122a and 122b for forming a dissecting section 112.

Figure 18:
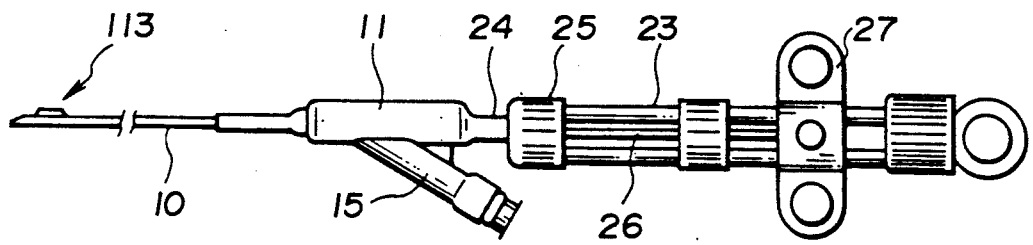
Figure 19:
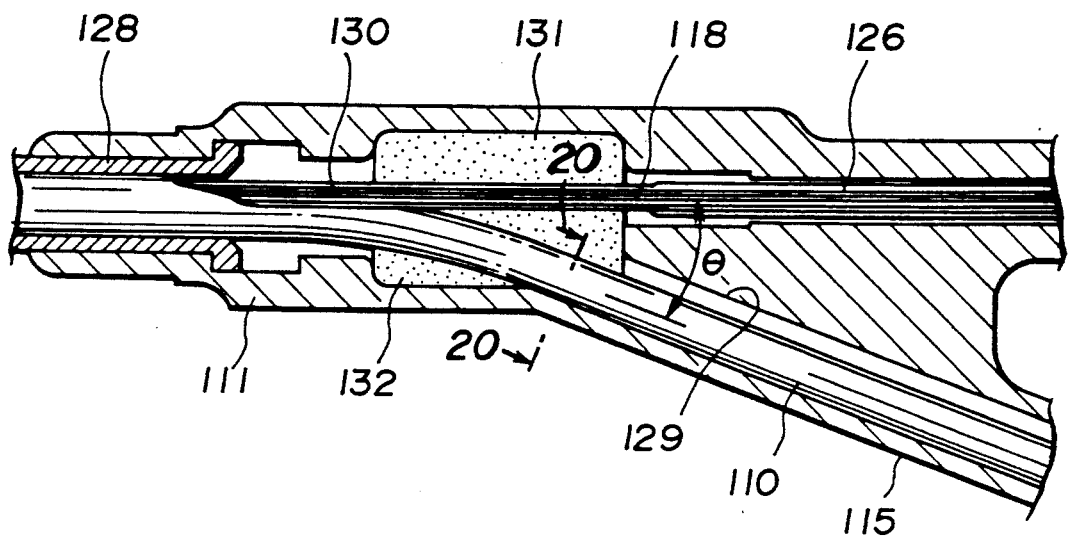

As shown in FIG. 18, a bifurcating section 11 is connected to the proximal portion of a flexible sheath 10. The back of the bifurcating section 11, from which the flexible sheath 10 is extending backward, is connected with an operation handle 23. As shown in FIG. 19, a branch 115 is branching out to form a certain angle with respect to the direction in which the operation handle 23 is connected. The angle is determined so that the branch 15 will not interfere with a fixing ring 25 clamping the tip of the operation handle 23.

In the operation handle 23, the back 24 of the bifurcating section 11 and an operation rod 26 extending from the back 24 are connected to the fixing ring 25 and to a slider 27.

As shown in FIG. 19, in a bifurcating section 111, a flexible sheath 110 is fixed to a tube coupler 128 in the distal portion of the bifurcating section 111. The flexible sheath 110 is curved in the vicinity of the back of the tube coupler 128 to form a bifurcation angle, then branches out as a branch 115. In this state, the flexible sheath 110 is processed secondarily so that the flexible sheath 110 will have different cross-sectional shapes between the points forward and backward of the tube coupler 128. Specifically, the cross section of the sheath 110 at a point forward of the tube coupler 128 is circular or expressed as an outer circle in FIG. 16, while the cross section of the sheath 110 at a point backward of the tube coupler 128 looks like FIG. 20 in which the portion of the first lumen 117 is missing (cut out).

Figure 20:
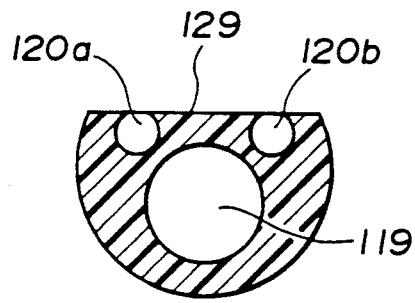

In FIG. 20, the branch 115 branching out from the bifurcating section 111 has a cut plane attributable to the fact that part of the sheath 110 corresponding to the first lumen 117 is missing in the axial direction. In the bifurcating section 111, therefore, the cut plane 129 is positioned on the opposite side of the center of curvature of bending.

Furthermore, a guide pipe 130 runs steadily from the back portion of the tube coupler 128 through the first lumen 117 in the flexible sheath 110 along the cut plane 129. A conducting wire 118 running through the guide pipe 130 is guided to the back 24 of the bifurcating section 111. Then, the guide pipe 130 is fixed to the end of an operation rod 26. The operation rod 26 can slide on the circumferential surface of the guide pipe 130.

A bifurcation housing 131 in the bifurcating section 111 is filled with bond 132, thus securing the flexible sheath 110 and guide pipe 130. The bond 132 reinforces the cut plane of the flexible sheath 110.

For example, in FIG. 16, a first lumen 117 and two lumens 120a and 120b have the same inner diameter; such as, 0.45 mm. A wire 118 having an outer diameter of 0.20 mm is routed through the first lumen 117. The inner diameter of the second lumen 119 is 1.1 mm.

A guide pipe 126 in FIG. 19, which is connected to a first lumen 117 in a bifurcating section 111, has an inner diameter of, for example, 0.25 mm.

It is preferred that the outer diameter of the wire 118 is 0.20 mm and the inner diameter of the guide pipe 126 is 0.25 mm. However, the outer diameter of the wire and the inner diameter of the guide pipe 127 are not restricted to the above values. Any values can be set under the condition that the outer diameter of the wire be at least 50% of the inner diameter of the guide pipe 126.

Next, the operation of the fifth embodiment having the aforesaid configuration will be described.

Dissection of the duodenal papilla or an example of treatment using a diathermic dissector can be carried out as described in conjunction with FIG. 11. The diathermic dissector is guided in the bile duct 41 with the help of a guide wire 42. After the guide wire 42 is removed, a slider 27 of an operation handle 23 is, for example, withdrawn to pull a conducting wire 118 along a flexible sheath 110 towards the proximal side.

Figure 21:
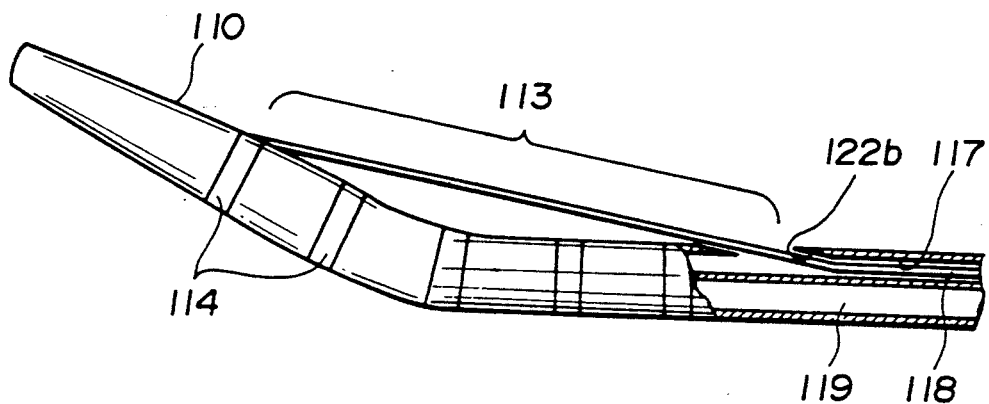

Then, a dissecting section 113 or a knife wire 112 coming out from the tip of the flexible sheath 110 curves to form an arc as shown in FIG. 21. The knife wire 112 projects to form a knife-like shape. With the knife wire 112 pressed on the papilla, high-frequency current is supplied to flow through the conducting wire 118. Thus, the papilla is dissected.

In this embodiment, a flexible sheath 110 has two lumens 120a and 120b as well as a first lumen 117 for guiding the conducting wire 118 and a second lumen 119. These two lumens 120a and 120b improves flexibility of the flexible sheath 110. Therefore, only a limited force is required to curve the distal portion of the sheath 110 in which the incising section 113 is formed. Thus, with a limited force, the knife wire 112 or the conducting wire 118 can be projected to form an easy-to-operate shape.

When the guide wire is guided out of the tip of the second lumen 119 in the flexible sheath 110, the guide wire passes through a curved area in a bifurcating section 111 in the flexible sheath 110. Even in the curved area, the guide wire will not pierce a cut plane 129 but pass through the bifurcating section 111 smoothly. This is because a bifurcation housing 131 of the bifurcating section 111 is filled with bond 132 which duly reinforce the cut plane 129.

The fifth embodiment has the advantages the first embodiment provides. In addition, since a sheath 110 has higher flexibility, only a limited force is required to curve part of a sheath corresponding to a dissecting section 113 formed in the distal portion of the sheath 110. Therefore, a wire 118 can be projected to form a shape most suitable for dissection, as shown in FIG. 21, with a small tensile force. This results in improved durability of the wire 118 and higher operability.

Figure 22:
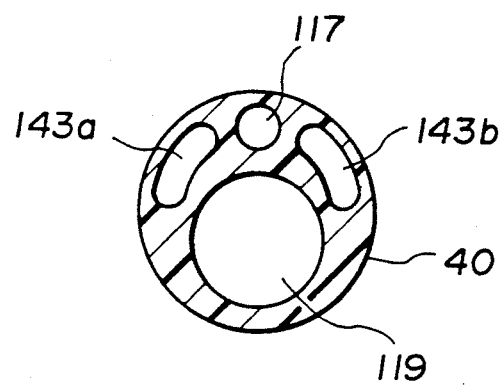

FIG. 22 shows the cross section of the distal portion of a sheath 110 in a variant of the fifth embodiment of the present invention.

In this variant, a flexible sheath 40 is provided with a first lumen 117 and a second lumen 119. Two lumens 143a and 143b formed in addition to these lumens 117 and 119 have different cross-sectional shapes from those in the fifth embodiment.

More specifically, two lumens 143a and 143b, which are formed by boring the wall of the sheath to improve the flexibility of the sheath, have, for example, symmetrical substantially-elliptic cross-sectional shapes. These two lumens 143a and 143b have maximum sizes within a range that the lumens 1431 and 143b as well as other lumens 117 and 119 will not cause any cracks (or the lumens 143a and 143b will not crack the wall to communicate with other lumens 117 and 119).

Thus, two lumens 143a and 143b are created with maximum possible sizes additionally to a first lumen 117 and a second lumen 119. This further improves the flexibility of a flexible sheath 140. Consequently, part of the sheath 140 corresponding to a dissecting section 113 can be curved with a limited force.

Other components and operation are identical to those of the fifth embodiment. The description will be omitted.

Two lumens other than a first lumen and a second lumen need not extend over the whole length of a sheath, but may be created in part of the sheath corresponding to a dissecting section or an extracted conducting wire.

Figure 23:
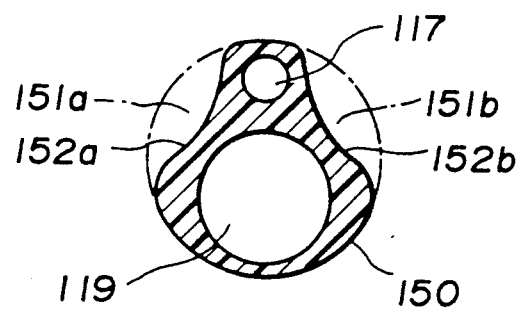
FIG. 23 is a cross-sectional diagram of the distal portion of a sheath in the sixth embodiment of the present invention.

FIG. 23 shows the cross-sectional shape of the distal portion of a sheath 150 in the sixth embodiment of the present invention. As shown in FIG. 23, the distal portion of the sheath 150 of this embodiment has a first lumen 117 and a second lumen 119. Circumferential portions of the sheath 150 are cut out symmetrically with respect to a line linking between the centers of the first lumen 117 and second lumen 119 to form cutouts (or notches) 151a and 151b. These cutouts 151a and 151b are formed to reduce the cross-sectional area of the wall of the sheath (portion indicated with a dot-dash line in FIG. 23), thus improving the flexibility of the sheath.

In the embodiment of FIG. 23, the cutouts 151a and 151b have streamlined surfaces 152a and 152b, so that body fluid will hardly adhere to the surfaces when a sheath is guided in a body cavity. Even if body fluid adheres to the surfaces 152a and 152b, the body fluid can be washed away effortlessly.

Therefore, if a sheath is made of material resistive to body fluid, stepped cutouts or notches may be formed. That is to say, the shapes of cutouts are not restricted to those of cutouts 151a and 151b.

The aforesaid embodiments may be combined partly to form other different embodiments which also belong to the present invention.

What is claimed is:

1. A diathermic dissector, comprising:
   a sheath having flexibility and including a first lumen and a second lumen which are made of insulating material;
   a conducting wire member running through said first lumen, exposing itself outside at openings formed in the terminal portion of said first lumen, and forming in the terminal portion of said first lumen, and forming a dissecting section for dissecting a contact tissue with supplied high-frequency current supplied;
   a bifurcating section formed in the proximal portion of said sheath to bifurcate said sheath into a first path having substantially the same cross-sectional area as said first lumen and communicating with said first lumen for guiding said wire member, a second path communicating with said second lumen, said second path and said second lumen formed as a single unit;
   a guide pipe connected to a proximal portion of said first lumen through an inside of said first lumen in said bifurcating section, an inside diameter of said guide pipe having substantially the same area as that of said first lumen, said guide pipe guiding said wire member; and an operation member inserted into said first path and slidable into said guide pipe, a proximal portion of said operation member connected to the proximal portion of said wire member for advancing or withdrawing said wire member in the longitudinal direction of said sheath.

2. A diathermic dissector according to claim 1 further comprising a third lumen in addition to said first lumen and said second lumen formed in the wall of said sheath having said openings.

3. A diathermic dissector according to claim 2 wherein said third lumen includes a plurality of lumens.

4. A diathermic dissector according to claim 3 wherein said plurality of lumens are mutually symmetrical with respect to a line linking between the centers of said first lumen and said second lumen.

5. A diathermic dissector according to claim 2 wherein said third lumen has a circular cross section.

6. A diathermic dissector according to claim 2 wherein said third lumen has an almost elliptic cross section.

7. A diathermic dissector according to claim 1 wherein said second path is oriented to a direction different from the longitudinal direction of said sheath at said bifurcating section.

8. A diathermic dissector according to claim 7 wherein said second path is reinforced with reinforcing member in said bifurcating section.

9. A diathermic dissector according to claim 1 wherein said first path is oriented to a direction in parallel with the longitudinal direction of said sheath at said bifurcating section.

10. A diathermic dissector according to claim 1 wherein the circumferential surface of said sheath between two openings or a portion forming said dissecting section has marks for indicating lengths.

11. A diathermic dissector according to claim 1 wherein the end of said guide pipe is pressed into an opening at the proximal end of said first lumen.

12. A diathermic dissector according to claim 1 wherein the end of said guide pipe is adhered to an opening at the proximal end of said first lumen.

13. A diathermic dissector according to claim 1 wherein the end of first lumen for guiding said wire member is blocked with a blocking member.

14. A diathermic dissector according to claim 1 wherein the terminal portion of said sheath is tapered and the end of said sheath opens with almost the same cross-sectional shape as said second lumen.

15. A diathermic dissector according to claim 1 wherein the proximal end of said second path is provided with a base for supplying fluid.

16. A diathermic dissector according to claim 1 further comprising a cutout for reducing the cross-sectional area of the wall of said sheath having said openings.

17. A diathermic dissector according to claim 2 or 16 wherein said third lumen or said cutout improves the flexibility of a sheath portion in which said openings are formed.

18. A diathermic dissector according to claim 1 wherein said first lumen has a smaller cross-sectional area than said second lumen.

19. A diathermic dissector according to claim 1 wherein said first lumen is coupled to said first path.

20. A diathermic dissector according to claim 19 wherein said second lumen is coupled to said second path.

21. A diathermic dissector according to claim 1 wherein said sheath can run through a channel of an endoscope.

22. A diathermic dissector according to claim 1 wherein said wire has an outer diameter of about 0.2 mm when said first lumen has an inner diameter of about 0.45 mm.

23. A diathermic dissector according to claim 1 wherein said guide pipe has an inner diameter of about 0.20 mm when said first lumen has an inner diameter of about 0.45 mm.

24. A diathermic dissector according to claim 1 wherein the outer diameter of said first lumen is at least 50% of the inner diameter of said guide pipe.

25. A diathermic dissector according to claim 1 wherein said first path formed in said bifurcating section has a hollow path which opposes an opening formed in the proximal portion of said first lumen and has almost the same cross-sectional area as that of the bore of said first lumen.

26. A diathermic dissector according to claim 1 wherein said first path is formed by branching out the proximal portion of part of said sheath corresponding to said first lumen within said bifurcating section.

27. A diathermic dissector according to claim 26 wherein said first path has the same inner diameter as said first lumen.

28. A diathermic dissector according to claim 1 wherein said first path has a guide groove into which a distal end of said operation member is insertable.

29. A diathermic dissector according to claim 1 wherein said bifurcating section has a greater cross section than respective cross sections of said first and second lumens.

30. An endoscope system, comprising:
a diathermic dissector including:
a sheath having flexibility and including a first lumen and a second lumen which are made of insulating material;
a conducting wire member running through said first lumen, exposing itself outside at openings formed in the terminal portion of said first lumen, and forming a dissecting section for dissecting a contact tissue with supplied high-frequency current;
a bifurcating section formed in the proximal portion of said sheath to bifurcate said sheath into a first path having substantially the same cross-sectional area as said first lumen and communicating with said first lumen for guiding said wire member, and a second path communicating with said second lumen, said second lumen formed as a single unit;
a guide pipe connected to a proximal portion of said first lumen through an inside of said first lumen in said bifurcating section, an inside diameter of said guide pipe having substantially the same area as that of said first lumen, said guide pipe guiding said wire member; and
an operation member inserted into said first path and slidable into said guide pipe, a proximal portion of said operation member connected to the proximal portion of said wire member for advancing or withdrawing said wire member in the longitudinal direction of said sheath;
an endoscope including:
an elongated insertion tube;

a channel running through said insertion tube for guiding said sheath; and an observation window and an illumination window which are formed at the distal end of said insertion tube; and a light source for supplying illumination light to said endoscope.

* * * * *